United States Patent [19]

Cottingham

[11] Patent Number: 4,596,695

[45] Date of Patent: Jun. 24, 1986

[54] AGGLUTINOGRAPHIC REACTION CHAMBER

[76] Inventor: Hugh V. Cottingham, 49 Mountain Ave., Caldwell, N.J. 07006

[21] Appl. No.: 648,912

[22] Filed: Sep. 10, 1984

[51] Int. Cl.⁴ ............................................. G02B 21/34
[52] U.S. Cl. ...................................... 422/58; 422/101; 422/102
[58] Field of Search ......................... 422/58, 101, 102; 356/246; 350/534, 536; 73/864.72, 864.02

[56] References Cited

U.S. PATENT DOCUMENTS 4,022,521  5/1977  Hall et al. ............................ 350/536
4,088,448  5/1978  Lilja et al. ............................. 422/58
4,171,866  10/1979 Tolles .................................... 350/536

Primary Examiner—Frank Sever
Attorney, Agent, or Firm—Blum Kaplan Friedman Silberman & Beran

[57] ABSTRACT

An agglutinographic reaction chamber for reacting immunochemical particle reagents. The chamber includes a first transparent panel having a first surface and a second panel having a second surface spaced apart from the first surface to define a chamber therebetween. The chamber intrinsically causes immunochemical particle reagents to react by being moved therein without external motion being imparted to the chamber.

29 Claims, 16 Drawing Figures

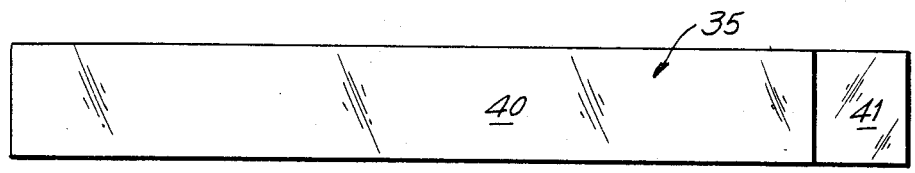
FIG.4
FIG.5
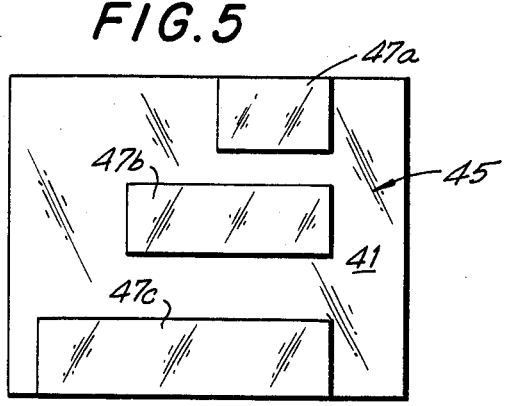
FIG.7
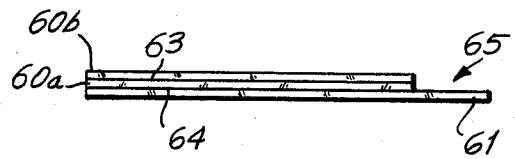
FIG.6A
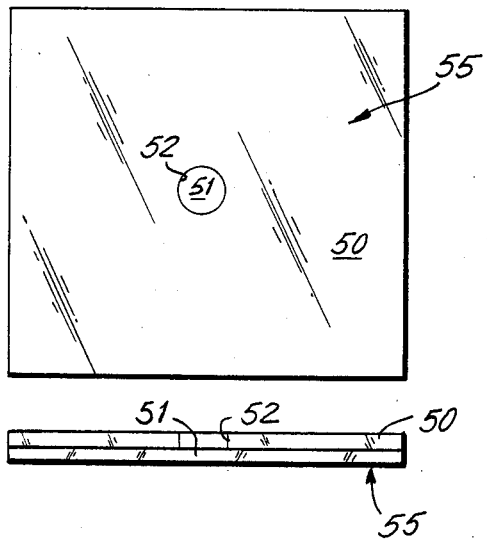
FIG.6B
FIG.8A
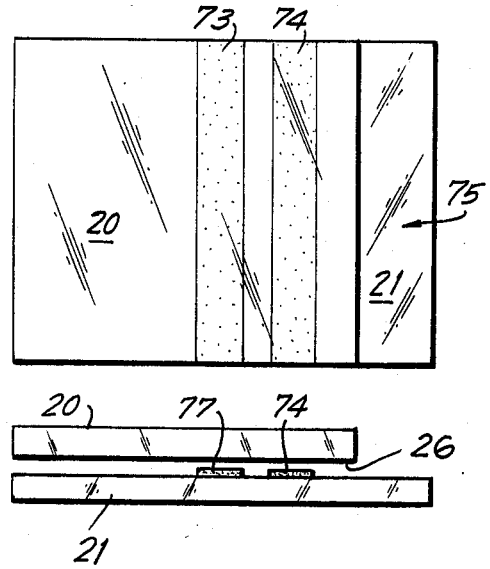
FIG.8B

AGGLUTINOGRAPHIC REACTION CHAMBER

The invention is generally directed to the reaction of immunochemical particle reactions and in particular to an agglutinographic reaction chamber which intrinsically causes agglutination of immunochemical particle reagents and presents a stable, high contrast visual record of the agglutination reaction. The process by which a stable, high contrast visual record of an immunochemical particle agglutination reaction occurs, without the necessity of external movement, is referred to herein as "agglutinography" or an "agglutinographic reaction."

Methods for reacting immunochemical particle reagents using laboratory slides are well known but have less than satisfactory results. These known methods are usually characterized by the placement of liquid reagents on a glass slide and a gentle rocking and swirling of the slide to cause the liquid reagents to swirl around and form agglutinations. Without the swirling of the particle reagents visible agglutinations are not reliably formed.

Typically, to obtain optimum performance the rocking and swirling of the slide must be performed in an exact manner, for a precise period of time. At the end of the rocking and swirling period the results must be read immediately. This known method produces incorrect results under several conditions. If the swirling is performed to quickly or too slowly or if the rocking and swirling time is too short or too long the reagents will either not react completely or react too much. If the results of the reaction are not observed at the end of the rocking time it could continue to react. Conventional agglutination reagents also evaporate in a matter of minutes thereby rapidly destroying the visual record of the particular reaction. If the reagents spill off the edges of the slide during rocking, or other handling, inaccurate results will naturally follow.

SUMMARY OF THE INVENTION

An agglutinographic reaction chamber for liquid particle reagents is provided. The reaction chamber is comprised of a first panel and a second panel overlapping at least part of the first panel. The non-overlapping area of the first panel defines a receiving region. The first panel is separated from the second panel at a predetermined distance to define a chamber between said first and second panels. Introduction of liquid particle reagents at or about the receiving region causes a capillary force to move the liquid reagents into the chamber and causes an agglutination reaction to occur between the first and second panels.

It is an object of the invention to provide an agglutinographic reaction chamber.

Another object of the invention is to provide an agglutinographic reaction chamber which causes agglutinations to form without rocking or swirling.

Yet another object of the invention is to provide an agglutinographic reaction chamber which causes agglutinations to form that are reproducible and easily observed without the need to time the reaction.

Still another object of the invention is to provide an agglutinographic reaction chamber which produces a record of the agglutinographic reaction.

A further object of the invention is to provide an agglutinographic reaction chamber which is simple to use and generates reproducible agglutination reactions.

Still other objects and advantages of the invention will in part be obvious and will in part be apparent from the specification.

BRIEF DESCRIPTION OF THE DRAWINGS

For a fuller understanding of the invention, reference is had to the following description taken in connection with the accompanying drawings, in which:

FIG. 4 is an alternate embodiment of an agglutinographic reaction chamber constructed in accordance with the invention;

FIG. 5 is a further embodiment of an agglutinographic reaction chamber constructed in accordance with the invention;

FIG. 6A is a top plan view of another embodiment of an agglutinographic reaction chamber constructed in accordance with the invention;

FIG. 6B is a side elevational view of the agglutinographic reaction chamber of FIG. 6A;

FIG. 7 is a side elevational view of another embodiment of an agglutinographic reaction chamber constructed in accordance with the invention;

FIG. 8A is a top plan view of another embodiment of an agglutinographic reaction chamber constructed in accordance with the invention; and FIG. 8B is a side elevational view of the agglutinographic reaction chamber of FIG. 8A.

DETAILED DESCRIPTION OF THE PREFERRED EMBODIMENTS

Figure 1A:
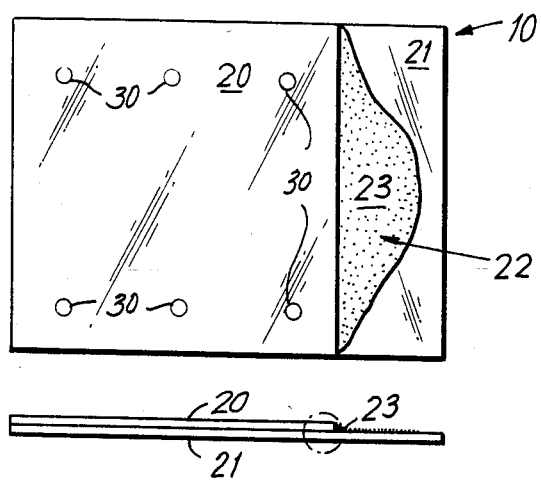
FIG. 1A is a top plan view of an agglutinographic reaction chamber constructed in accordance with a preferred embodiment of the invention.
Figure 1B:
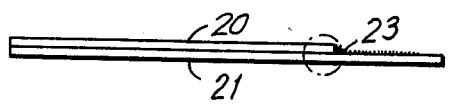
FIG. 1B is a side elevational view of the agglutinographic reaction chamber of FIG. 1A.
Figure 1C:
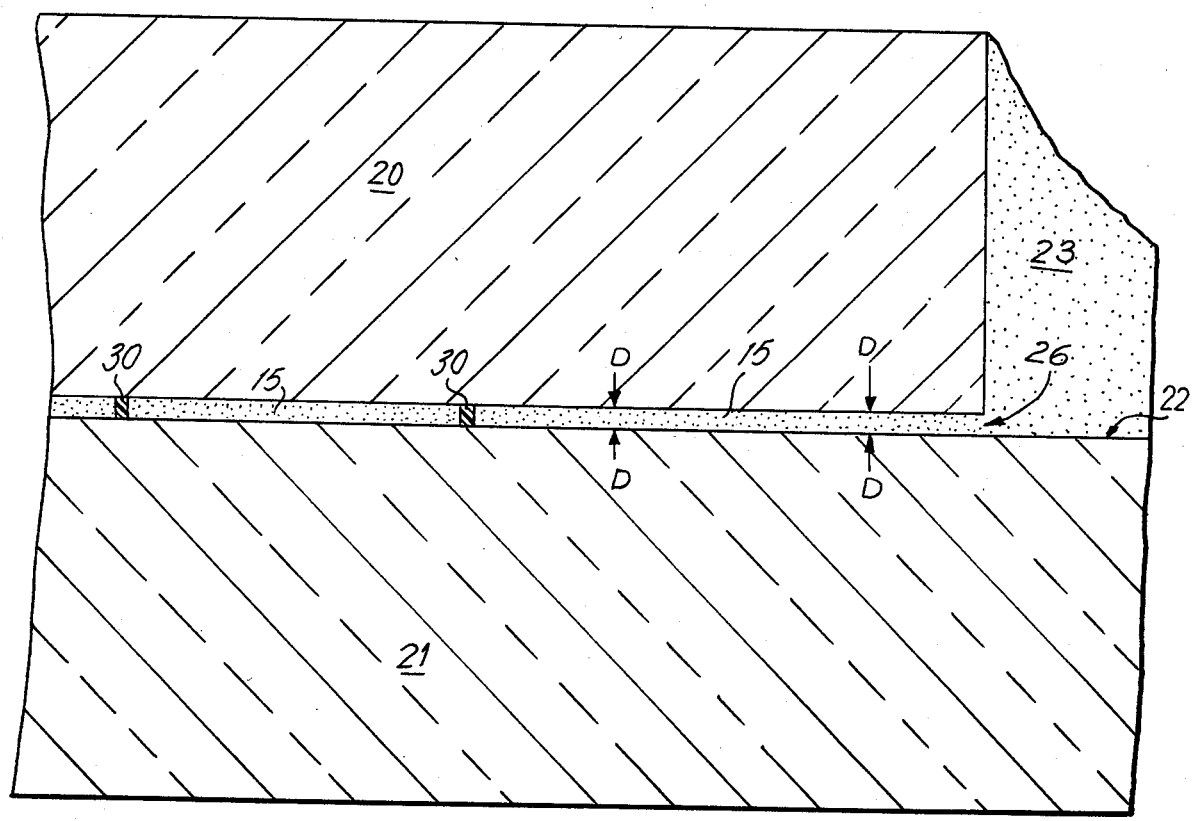
FIG. 1C is a partially enlarged view of circled region C of FIG. 1B.

Reference is first made to FIGS. 1A-1C wherein an agglutinographic reaction chamber, generally indicated as 10, and constructed in accordance with the instant invention is depicted. Agglutinographic reaction chamber 10 is comprised of an upper panel of glass 20 and a lower panel of glass 21 with a narrow space D—D defined between panels 20, 21 bounded by spacers 30 to provide a planar capillary chamber 15. A receiving region 22 is defined by the area in which the smaller panel 20 does not overlap panel 21. Immunochemical particle reagents in a liquid 23 are applied to the receiving region 22. Reagents 12 are placed near the end 26 of capillary chamber 15. Immunochemical particle reagents 23 are then drawn into the capillary chamber 15 by capillary action and are caused to be drawn through the entire chamber. Panels 20, 21 may be of equal size and reagents 23 are then introduced at an entrance to capillary chamber 15.

In order to understand the manner in which an agglutination reaction test occurs using the agglutination reaction chamber of the instant invention, the following basic steps explain an agglutination test. A test sample, antibody reagent, and polystyrene latex reagent would be pipetted onto slide 10 at receiving region 22.

Reagents and test sample 23 are drawn through capillary chamber 15. If the test sample is absent the molecule of interest, the reagent sample begins to react and form small agglutinations. This capillary flow, which is intrinsic to the agglutinographic reaction chamber provides the driving force for the formation of agglutinations. As soon as two particles react to form an agglutination their combined velocity is reduced relative to the unreacted particles.

This reduction in velocity is predicted by Stokes' Law:

$$F = 6\pi n r v; v = F/6\pi n \times 1r$$

Stokes' Law states that for a particle in a liquid of viscosity n, the velocity v of the particle relative to the velocity of the liquid is inversely proportional to the radius r of the particle.

Accordingly, an agglutination of particles moves more slowly than unagglutinated particles. Likewise, larger agglutinations of particles move more slowly than smaller agglutinations of particles. Furthermore in the event that the molecule of interest is present, the agglutination reaction will react proportionally to the quantity of molecule of interest present.

With reference to FIGS. 1A-1C, as the liquid reagents move from right to left unreacted particles that are behind an agglutination collide with the agglutination because of the relative velocity difference existing between the unreacted particles and the agglutinated particles. These collisions result in even larger agglutinations which move even more slowly and are thus exposed to an ever increasing rate of collision with unreacted particles and smaller agglutinations.

This reactive process continues until the size of the agglutinations increase to the extent that their velocity approaches zero, at which point any unreacted particles either stick to the agglutination or continue on past the agglutinations in the liquid flux surrounding the agglutinated particles. The result of this situation is a very high contrast visual display of the agglutinations when they occur in the test sample.

Figure 2A:
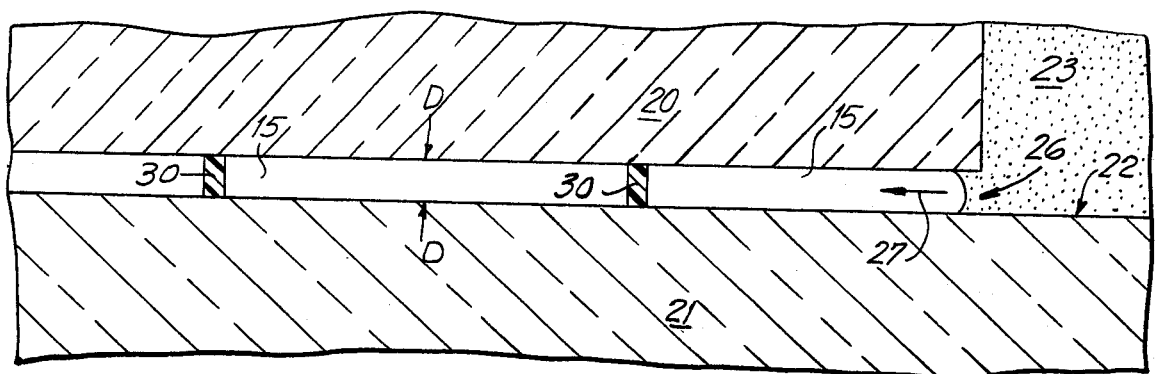
FIGS. 2A-2C are progressive cross-sectional views of an agglutinographic reaction occurring in the agglutinographic reaction chamber of FIG. 1A.
Figure 2B:
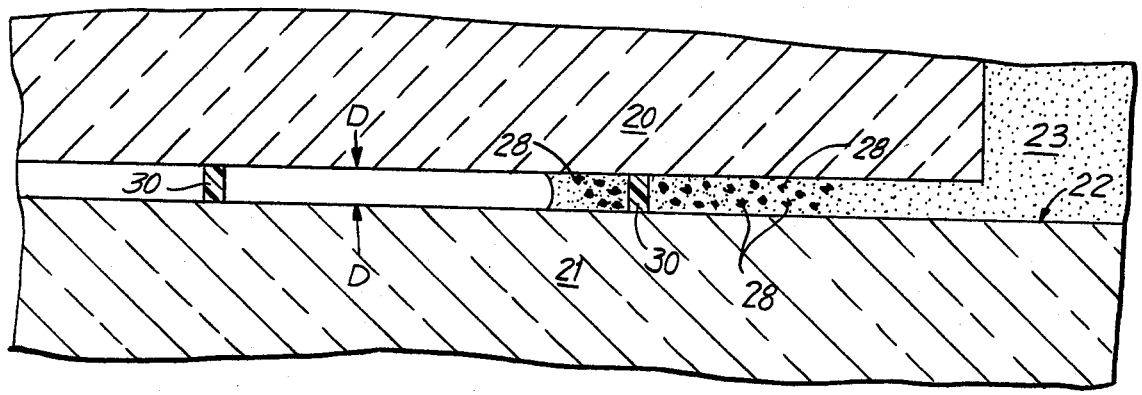
Figure 2C:
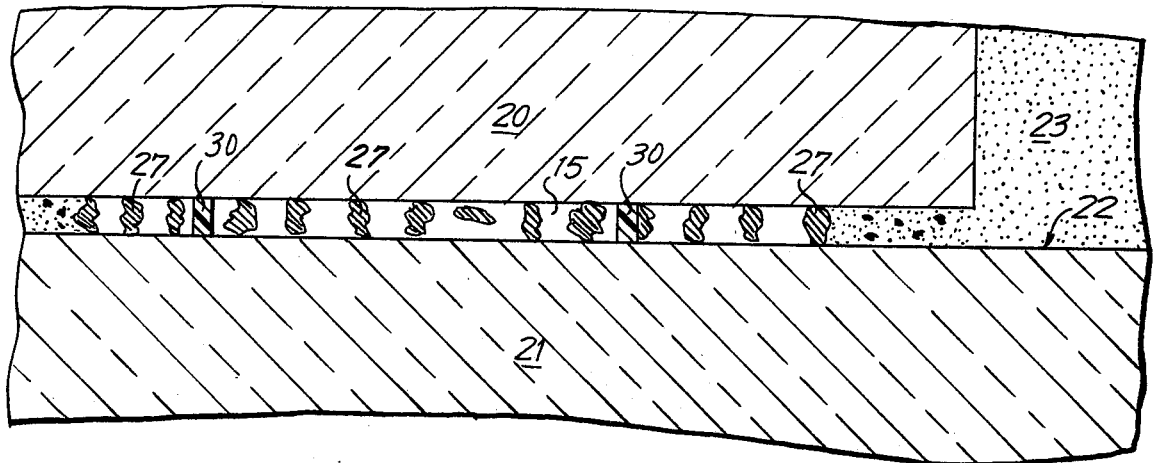
Figure 3A:
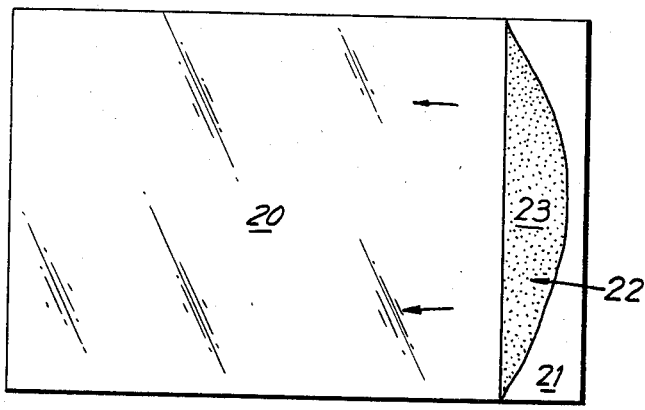
FIGS. 3A-3C are progressive top plan views of the agglutinographic reaction respectively depicted in FIGS. 2A-2C.

Reference is next made to FIGS. 2A-2C and 3A-3C wherein a sequential illustration of an agglutinographic reaction occurring in the agglutinographic reaction chamber of FIG. 1 is depicted. FIGS. 2A and 3A depict the condition of the reaction as the agglutinographic reagents 23 are pipetted onto receiving region 22 of panel 21 near the position 26 of capillary chamber 15. Reagent 22 is drawn by capillary action into capillary chamber 15. Liquid reagents 23 will be continuously drawn into capillary chamber 15 in the direction of arrow 27 until the far end of capillary chamber 15 is reached.

Figure 3B:
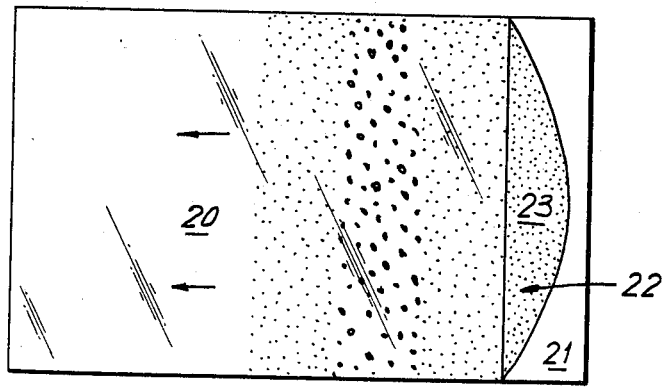

Reference is next made to FIGS. 2B and 3B wherein liquid reagents 23 have entered capillary chamber 15 and have begun to agglutinate into small agglutinations 26. As liquid reagents 23 are drawn into capillary chamber 15 a liquid flow in the direction of arrow 27 causes the agglutinographic particles in reagent 23 to begin to agglutinate into small agglutinations 28.

Figure 3C:
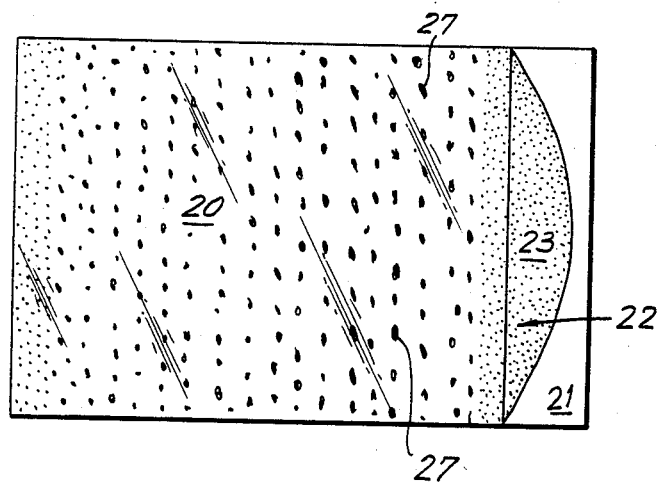

Reference is next made to FIGS. 2C and 3C wherein a completed agglutinographic reaction is depicted. The reaction terminates when the capillary forces cease to cause the reagents to flow and the agglutinographic reaction chamber visually stabilizes.

As can be seen more clearly in FIG. 3C, there is a very high degree of agglutination uniformly visible across the entire area of the capillary chamber.

Because the agglutinographic reaction is maintained between two glass panels 20,21 the liquid does not evaporate rapidly and the completed reaction remains stable. As a result it can be viewed over a much longer period of time than could the prior art, open air, agglutinographic reaction.

In a preferred embodiment of the invention as depicted in FIG. 1 an agglutinographic reaction chamber 10 is constructed as follows. Lower panel 21 and upper panel 20 are glass. Lower panel 21 is for example a 50 mm×50 mm by 1 mm glass slide and upper panel 20 is a 50 mm×40 mm×1 mm glass slide. These two glass panels are separated by a distance of about 3 microns to create capillary chamber 15. Reagent 23 is composed of a mixture of agglutination reagents such as 0.3 micron diameter polystyrene latex coated with HCG and an antibody to HCG in solution.

Panels 20 and 21 need not, of course, be in these dimensions or necessarily be made of glass. However, at least one of lower panel 21 and upper panel 20 must have a wettable surface forming a surface of capillary chamber 15.

Distance D—D between upper sheet 20 and lower sheet 21 can vary from approximately 0.1–500 microns, is preferably 2–20 microns, and more preferably 3–7 microns. The optimum distance D—D is dependent upon the size of the unreacted particles. The larger the unreacted particles, the larger distance D—D must be for are optimum agglutinographic reaction to occur. Likewise, smaller unreacted particles react more efficiently in capillary chamber 15 having a smaller distance D—D.

Distance D—D is maintained between upper panel 20 and lower panel 21 by spacers 30. A large number of different types of spacers can be used to maintain the spaced relationship between sheets 20, 21. Spacers 30 can either be paint, silkscreening, ink, polyester film, dust, surface irregularities on the slides or a discrete film. Various materials will yield optimal results depending upon the distance D—D to be used in a particular agglutinographic reaction chamber, the reagents to be used in the agglutinographic reaction chamber and manufacturing tolerances.

Reference is next made to FIG. 4 wherein an alternate embodiment of an agglutinographic reaction chamber, generally indicated as 35, constructed in accordance with the invention is depicted. Chamber 35 consists of an upper glass panel 40 and a lower glass panel 41 separated by a distance D—D. The embodiment of FIG. 4 is the same as the embodiment of FIGS. 1-3 except that upper and lower panels 40, 41 are longer than panels 20, 21. This extended distance provides for an increased path for the liquid to travel and a longer period of active reaction. With the longer slide a broader distribution of agglutinations is possible.

Reference is next made to FIG. 5 wherein an agglutinographic reaction chamber 45 constructed in accordance with another embodiment of the invention is depicted. Reaction chamber 45 consists of a single lower panel 41 having three upper panels 47a, 47b, 47c of different lengths. In all other functional aspects the embodiment of FIG. 5 is the same as the embodiment of FIG. 1. The use of three upper panels of differing lengths provides a display of differential degrees of agglutination for the same reagent. While the embodiment of FIG. 5 is shown with three upper panels 47a, 47b, 47c, two upper panels or four or more upper panels may be used depending upon varying requirements.

Reference is next made to FIGS. 6A, 6B wherein an agglutinographic reaction chamber, generally indicated as 55, constructed in accordance with another embodiment of the invention is depicted. In this case an upper panel 50 has a circular opening 52 at its center. The outside dimensions of top panel 50 and bottom panel 51 are the same.

In this embodiment the reagent is pipetted onto lower panel 51 through opening 52. This configuration provides for a radial pattern of agglutination and presents less of an opportunity to spill the reagents. Except for the location of the receiving region for the reagents this embodiment embodies the same funtional and structural features and benefits discussed above with respect to FIG. 1. In addition a radial distribution pattern is created.

Reference is next made to FIG. 7 wherein an agglutinographic reaction chamber, generally indicated as 65, constructed in accordance with another embodiment of the invention is depicted. Reaction chamber 65 has a lower panel 61 and an upper panel 60a both of which embody the same functional and structural features and benefits discused above with respect to FIG. 1. However, capillary chamber 65 also has a second upper panel 60b overlapping panel 60a and having the same length as panel 60a. In this way two layers of agglutination are visually superimposed for enhanced viewing of agglutination reactions. Spacers 63 are disposed between panels 60a and 60b and spacers 64 are disposed between panels 60a and 61 to maintain these three panels in spaced relation. Spacers 63 and 64 can be adjusted to create two capillary chambers of similar or different dimensions.

Reference is next made to FIGS. 8A, 8B wherein an agglutinographic reaction chamber, generally indicated as 75, constructed in accordance with another embodiment of the invention is depicted. The embodiment of FIGS. 8A, 8B is structurally similar to the embodiment of FIG. 1 like elements having like reference numerals. One or more bands of chemicals 73, 74 are placed between panels 20, 21 in the path of the liquid reagents within capillary chamber 15 to cause an additional desired effect. This additional desired effect may be either chemical or visual. It may be desirable to place one reagent in the agglutinographic reaction chamber and introduce another reagent at opening 26 of capillary chamber 15. This can obviate the need to mix reagents before introducing them into the reaction chamber. Several different chemicals can be used to ascertain if the liquid placed at the edge of the capillary plane agglutinates in the presence of different chemicals.

Accordingly, an agglutinographic reaction chamber is provided which: requires no rocking or swirling; proceeds automatically to the end of the reaction; prevents spillage of reagents; requires no monitoring of the reaction; and is visually stable for a long period of time because no significant evaporation.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is understood that the following claims are intended to cover all of the generic and specific features of the invention herein described and all statements of the scope of the invention which, as a matter of language, might be said to fall therebetween.

What is claimed is:

1. An agglutinographic reaction chamber for immunochemical liquid agglutination particle reagents comprising in combination a first transparent panel having a first wettable surface with a first predetermined area, a second panel having a second surface with a second predetermined area, said second surface is coextensive with and overlaps at least a portion of said first predetermined area, said second panel being spaced a predetermined distance of at least a range of 0.1 microns to 500 microns from said first panel so that said overlapping portion of said first and second surfaces define a capillary chamber for drawing liquid immunochemical particulate reagents between said overlapping portion of said first and second surfaces when said chamber is maintained substantially still, and causing an agglutination reaction to occur without rocking or swirling when such a liquid agglutination reagent is introduced at or about the capillary chamber to thereby produce a substantially reproducible record of an agglutination reaction without rocking or swirling said chamber.

2. The agglutinographic reaction chamber for liquid particle reagents of claim 1 wherein said second predetermined area is smaller than said first predetermined area, said non-overlapping area defined thereby defining a receiving region.

3. The agglutinographic reaction chamber of claim 1 wherein at least one of said first and second panels is a glass panel.

4. The agglutinographic reaction chamber of claim 1 wherein the first and second panels are both substantially planar glass panels.

5. The agglutinographic reaction chamber of claim 4 wherein the first and second panels have the same width and the first panel is longer than the second panel for forming a reagent receiving region on the first panel.

6. The agglutinographic reaction chamber of claim 5 wherein the liquid particle reagents are drawn into said capillary chamber by introducing said reagents at said receiving region.

7. The agglutinographic reaction chamber of claim 1 wherein said first and second panels are separated at said predetermined distance by spacer means.

8. The agglutinographic reaction chamber of claim 7 wherein the spacer means is a material selected from the group consisting of paint, silk screening, ink, film and dust.

9. The agglutinographic reaction chamber of claim 7 wherein the spacer means separates the first panel from the second panel by a predetermined distance within the range of 2 microns to 20 microns.

10. The agglutinographic reaction chamber of claim 7 wherein the spacer means separates the first panel from the second panel by a predetermined distance within the range of 3 microns to 7 microns.

11. The agglutinographic reaction chamber of claim 7 wherein the first panel is a glass slide 50 mm×40 mm×1 mm and the second panel is a glass slide 50 mm×40 mm×1 mm.

12. The agglutinographic reaction chamber of claim 1 wherein the first and second panels have the same width and the first panel is longer than the second panel, the length of the second panel is substantially greater than the width of the second panel.

13. The agglutinographic reaction chamber of claim 1 wherein said second panel comprises a plurality of panel members.

14. The agglutinographic reaction chamber of claim 13 wherein the plurality of panel members are glass slides.

15. The agglutinographic reaction chamber of claim 13 wherein said plurality of panels are rectangular solids of different lengths.

16. The agglutinographic reaction chamber of claim 1 wherein the second panel has an opening substantially in its center, said opening overlapping the first panel.

17. The agglutinographic reaction chamber of claim 16 wherein the opening in the second panel is a circular aperture.

18. The agglutinographic reaction chamber of claim 17 wherein the outside dimensions of the second panel are the same as the outside dimensions of the first panel.

19. The agglutinographic reaction chamber of claim 16, wherein the first surface is substantially circular and the second surface is substantially annular.

20. The agglutinographic reaction chamber of claim 1 further including a third panel on the opposite surface of the second panel than the first panel, said second panel further including a third surface with a third predetermined area, said third panel having a fourth surface with a fourth predetermined area, and said fourth surface is coextensive with and overlaps at least a second portion of said third surface, said third panel being spaced a second predetermined distance from said second panel so that said overlapping second portion of said third and fourth surfaces defines a second capillary chamber for drawing reagent liquids between said third and fourth surfaces when a reagent liquid is introduced at or about the second capillary chamber.

21. The agglutinographic reaction chamber of claim 20 wherein said first and second panels are separated at said predetermined distance by first spacer means.

22. The agglutinographic reaction chamber of claim 21 wherein the third panel is spaced the second predetermined distance from the second panel by second spacer means.

23. The agglutinographic reaction chamber of claim 22 wherein said first and second spacer means space the first and second and third and fourth surfaces substantially equal distances apart.

24. The agglutinographic reaction chamber of claim 22 wherein said first and second spacer means are materials selected from the group consisting of paint, silk screening, ink, film and dust.

25. The agglutinographic reaction chamber of claim 20 wherein the third and fourth predetermined areas are substantially equal.

26. The agglutinographic reaction chamber of claim 20 wherein said second, third and fourth predetermined areas are substantially equal.

27. The agglutinographic reaction chamber of claim 1 further including reaction means between said first panel and said second panel.

28. The agglutinographic reaction chamber of claim 1 wherein the liquid particle reagents are a mixture of polystyrene latex coated with HCG and an antibody to HCG in solution.

29. The agglutinographic reaction chamber of claim 28 wherein the polystyrene latex has a 0.3 micron diameter.

* * * * *